US012213771B2

(12) United States Patent
Curran et al.

(10) Patent No.: US 12,213,771 B2
(45) Date of Patent: *Feb. 4, 2025

(54) THERMISTOR IMBEDDED THERAPEUTIC CATHETER

(71) Applicants: ABIOMED, Inc., Danvers, MA (US); Icahn School of Medicine at Mount Sinai, New York, NY (US)

(72) Inventors: Jerald Wayne Curran, North Andover, MA (US); Kiyotake Ishikawa, Fort Lee, NJ (US); Roger J. Hajjar, Tenafly, NJ (US)

(73) Assignees: Abiomed, Inc., Danvers, MA (US); Icahn School of Medicine at Mount Sinai, New York, NY (US)

( * ) Notice: Subject to any disclaimer, the term of this patent is extended or adjusted under 35 U.S.C. 154(b) by 305 days.

This patent is subject to a terminal disclaimer.

(21) Appl. No.: 17/673,255

(22) Filed: Feb. 16, 2022

(65) Prior Publication Data
US 2022/0273935 A1 Sep. 1, 2022

Related U.S. Application Data

(63) Continuation of application No. 15/927,273, filed on Mar. 21, 2018, now Pat. No. 11,285,310.
(Continued)

(51) Int. Cl.
*A61M 60/585* (2021.01)
*A61B 5/00* (2006.01)
(Continued)

(52) U.S. Cl.
CPC .......... *A61B 5/029* (2013.01); *A61B 5/02028* (2013.01); *A61B 5/02141* (2013.01);
(Continued)

(58) Field of Classification Search
CPC ..................... A61B 5/029; A61M 60/585
(Continued)

(56) References Cited

U.S. PATENT DOCUMENTS 4,901,734 A 2/1990 Griffin et al.
5,046,505 A 9/1991 Sekii et al.
(Continued)

FOREIGN PATENT DOCUMENTS

EP 1588661 A1 10/2005
EP 2962720 A1 1/2016
(Continued)

OTHER PUBLICATIONS

Office Action from corresponding Korean Patent Application No. 10-2023-7020309 dated Aug. 3, 2023 (6 pp.).
(Continued)

*Primary Examiner* — Nicole F Lavert
(74) *Attorney, Agent, or Firm* — Botos Churchill IP Law LLP

(57) ABSTRACT

A system and method for determining native cardiac output of a heart while maintaining operation of an intracardiac blood pump includes determining a current drawn by the pump motor, a blood pressure within the ascending aorta, and a change in the blood temperature based on a thermodilution technique. An intracardiac blood pump positioned in the aorta includes at least one sensor for determining a motor current and blood pressure and a thermistor for determining the change in blood temperature after a precise fluid bolus has been introduced into the vasculature. A processor receives current, pressure, and temperature measurements, and calculates a pump flow output and a total cardiac output from which the native cardiac output is calculated. The native cardiac output and other clinically relevant variables derived from the measurements inform
(Continued)

decisions related to continued therapeutic care, including increasing or decreasing cardiac assistance provided by the intracardiac pump.

20 Claims, 13 Drawing Sheets

Related U.S. Application Data

(60) Provisional application No. 62/474,278, filed on Mar. 21, 2017.

(51) Int. Cl.
| | |
|---|---|
| *A61B 5/02* | (2006.01) |
| *A61B 5/021* | (2006.01) |
| *A61B 5/0215* | (2006.01) |
| *A61B 5/028* | (2006.01) |
| *A61B 5/029* | (2006.01) |
| *A61M 60/13* | (2021.01) |
| *A61M 60/135* | (2021.01) |
| *A61M 60/148* | (2021.01) |
| *A61M 60/205* | (2021.01) |
| *A61M 60/216* | (2021.01) |
| *A61M 60/50* | (2021.01) |
| *A61M 60/515* | (2021.01) |
| *A61M 60/531* | (2021.01) |
| *A61M 60/538* | (2021.01) |
| *A61M 60/816* | (2021.01) |
| *A61M 60/00* | (2021.01) |

(52) U.S. Cl.
CPC ............ *A61B 5/0215* (2013.01); *A61B 5/028* (2013.01); *A61B 5/6852* (2013.01); *A61M 60/13* (2021.01); *A61M 60/135* (2021.01); *A61M 60/148* (2021.01); *A61M 60/205* (2021.01); *A61M 60/216* (2021.01); *A61M 60/50* (2021.01); *A61M 60/515* (2021.01); *A61M 60/531* (2021.01); *A61M 60/538* (2021.01); *A61M 60/585* (2021.01); *A61M 60/816* (2021.01); *A61M 60/00* (2021.01)

(58) Field of Classification Search
USPC ............................................................ 600/5
See application file for complete search history.

(56) References Cited

U.S. PATENT DOCUMENTS

| | | | |
|---|---|---|---|
| 5,722,930 A * | 3/1998 | Larson, Jr. ............ | F16C 19/525 |
| | | | 600/16 |
| 5,911,685 A | 6/1999 | Siess et al. | |
| 5,964,694 A | 10/1999 | Siess et al. | |
| 6,139,487 A | 10/2000 | Siess | |
| 2001/0037048 A1 | 11/2001 | Pfeiffer et al. | |
| 2002/0151761 A1 | 10/2002 | Viole et al. | |
| 2003/0125774 A1* | 7/2003 | Salo ................... | A61N 1/3655 |
| | | | 607/21 |
| 2007/0287929 A1 | 12/2007 | Goedje et al. | |
| 2010/0268334 A1 | 10/2010 | Pate et al. | |
| 2016/0089035 A1* | 3/2016 | Jurek ................... | A61B 5/026 |
| | | | 600/365 |
| 2016/0287096 A1 | 10/2016 | Zhang | |

FOREIGN PATENT DOCUMENTS

| | | |
|---|---|---|
| JP | S63216540 A | 9/1988 |
| JP | 2000512191 A | 9/2000 |
| JP | 2004073875 A | 3/2004 |
| JP | 2005517502 A | 6/2005 |
| JP | 2007283109 A | 11/2007 |
| KR | 20170029555 A | 3/2017 |
| WO | 9843688 A1 | 10/1998 |
| WO | 2016001439 A1 | 1/2016 |
| WO | 2016001440 A1 | 1/2016 |

OTHER PUBLICATIONS

International Search Report PCT/US2018/023539 dated Jun. 6, 2018 (6 pages).
Office Action from corresponding Japanese Patent Application No. 2019-552617 dated Mar. 2, 2022 (10 pages).
Office Action from corresponding Australian Application No. 2018239421 dated Mar. 15, 2022 (3 pages).
Written Opinion issued in corresponding Singapore Application No. 11201908668Y dated Dec. 7, 2020 (6 pages).
Office Action issued in corresponding Indian Patent Application No. 201917041241 dated Feb. 22, 2023 (8 pp.).
Office Action for corresponding Israeli Application No. 269446 dated Jun. 7, 2022 (3 pages).
Office Action for corresponding Korean Application No. 10-2019-7030974 dated Jul. 13, 2022 (14 pages).
Written Opinion issued in corresponding Singapore Application No. 11201908668Y dated Aug. 29, 2022, pp. 1-5.
Office Action from corresponding Israeli Patent Application No. 305706 dated May 13, 2024 (4 pp.).
Office Action from corresponding Japanese Patent Application No. 2022-179947 dated Sep. 9, 2024 (4 pp.).

* cited by examiner

| Variable | Measured or calculated Value |
|---|---|
| Reference CO (L/min) | 2.32 |
| Cardiac Output (L/min) | 2.34 |
| Mean Transit Time (sec) | 19.32 |
| Downslope Time (sec) | 15.63 |
| Intrathoracic Thermal Volume (mL) | 754 |
| Pulmonary Thermal Volume (mL) | 610 |
| Extravascular Lung Water (mL) | 574 |
| Cardiac Power Output (watts) | 0.41 |

| Variable | Measured or calculated Value |
|---|---|
| Reference CO (L/min) | 6.04 |
| Cardiac Output (L/min) | 5.72 |
| Mean Transit Time (sec) | 7.04 |
| Downslope Time (sec) | 4.88 |
| Intrathoracic Thermal Volume (mL) | 671 |
| Pulmonary Thermal Volume (mL) | 465 |
| Extravascular Lung Water (mL) | 414 |
| Cardiac Power Output (watts) | 1.2 |

THERMISTOR IMBEDDED THERAPEUTIC CATHETER

CROSS REFERENCE TO RELATED APPLICATIONS

This application is a continuation of U.S. application Ser. No. 15/927,273, filed on Mar. 21, 2018, allowed, which application claims priority to U.S. provisional application No. 62/474,278, filed Mar. 21, 2017 and entitled "THERMISTOR IMBEDDED THERAPEUTIC CATHETER", the content of which is hereby incorporated herein by reference in its entirety.

BACKGROUND OF THE INVENTION

Cardiac output is a measure of the volume of blood the heart pumps through the circulatory system in a minute. However for patients who are on mechanical hemodynamic support, the cardiac output comprises two components: native cardiac output and a mechanical cardiac output. Native cardiac output refers to blood flow due to the function of the native heart, and mechanical cardiac output refers to the assistance in blood flow provided by an intracardiac mechanical device, such as a heart pump (e.g. an Impella 2.5 pump by Abiomed, Inc.). In a patient who is hemodynamically supported by a mechanical circulatory support device, native cardiac output is used to assess patient treatment and progress.

Measuring native cardiac output in patients requiring hemodynamic support poses technical and clinical difficulties using currently available technologies and approaches. Such techniques and technologies include: Doppler ultrasound, continuous wave Doppler, transesophageal Doppler, echocardiography, pulse pressure methods, calibrated pulse pressure, impedance cardiography, cardiac computed tomography, scintigraphy, magnetic resonance imaging, and thermodilution.

There are several notable issues with the currently available technology. First, each of the available technologies is only capable of measuring total cardiac output, and is unable to account for the continuous and differential flow through an active pump. In a cardiac output measurement obtained from a mechanically supported patient. Therefore, for these technologies to directly measure native cardiac output, the mechanical support must be temporarily discontinued or minimized such that the intracardiac device does not interfere with the measurement. Suspending the support would put the patient at unnecessary risk if native heart function is unable to provide sufficient cardiac output during the suspended period. These issues limit the usefulness of these technologies in treating a patient supported by a mechanical circulatory device. These technologies are limited in measuring native and total cardiac output instantaneously in a repeated and reproducible manner.

Other challenges are also prevalent. For example, it is clinically known that pulse pressure methods and echocardiography provide a less accurate estimate of cardiac output compared to thermodilution. Doppler-echocardiography is prone to interference from the pump flow. Cardiac computed tomography and scintigraphy expose patients to radiation, and repeat measurements with different flow to determine if the pump can be weaned is impractical using these modalities. Additionally, magnetic resonance imaging is incompatible with the mechanical support devices, while thermodilution in the right side heart requires obtaining another central vascular route which can increase the risk of vascular complications as well as infections. Placement of a Swan-Ganz catheter is sometimes difficult, can induce arrhythmia in patients with acute myocardial infarction, and requires X-ray to confirm the location once the catheter is moved.

BRIEF SUMMARY OF THE INVENTION

The methods and systems of the present disclosure addresses the above identified difficulties associated with the currently used methods, and to provide more accurate and useful information about heart function while the patient is on hemodynamic mechanical support. Further, this physiological information can provide the clinician with more insight into how the patient may respond when mechanical circulatory support is removed (weaning from support), allowing them to better predict patient response. This information is currently unavailable in the clinic.

Described herein are methods and systems for measuring one or more of total cardiac output, mechanical cardiac output, and native cardiac output. Example systems and methods use a thermistor imbedded in an intravascular blood pump, for example in the catheter sheath associated with the blood pump. The measurement of the native cardiac output may be made while continuing to provide mechanical support to the heart with the intravascular blood pump. The native cardiac output, as well as other variables derived from the native cardiac output measurement, may be displayed to a physician or pump operator in order to provide real-time information related to the status and condition of the heart.

In one aspect, a system is provided for measuring the performance of a beating heart. The system includes a sensor system, comprising at least one thermistor, for use in an intracardiac pump, the sensor system being configured to measure the cardiac output (one or more of total cardiac output, native cardiac output, and mechanical cardiac output) and optionally other physiologic parameters of the patient while the patient is on hemodynamic support. An example of a suitable intracardiac blood pump has a tubular cannula with proximal and distal openings, a cylindrical surface disposed between the proximal and distal openings and being configured to be positioned in the aorta, an electrically driven motor and a rotor disposed within the cannula, and an electrical line configured to supply current to the motor. A catheter may be provided, having proximal and distal end regions, the distal end region being connected to the cannula. A repositioning sheath may also be disposed about the catheter. A thermistor is disposed in the distal end region of the blood pump or in the catheter. The thermistor is configured to detect blood temperature flowing in the aorta of the heart. The system also provides a fluid source configured to provide a bolus, for example through a cold fluid source. The bolus can be of a suitable fluid at a predetermined temperature different than physiologic blood temperature (for example a temperature lower than blood temperature) that can thereby change the blood temperature in vasculature flowing into or away from the beating heart.

A plurality of sensors and a processor are used. The processor receives and processes one or more signals from the sensors. In addition to blood temperature sensors, other sensors can be deployed to measure other parameters. For example, a sensor may be used to detect the motor current, and another sensor detects the blood pressure within the heart. In an implementation, the processor is configured to receive a first signal from the motor current sensor, the first signal being indicative of a change in the motor current during operation. The processor also receives a second signal from the blood pressure sensor, the second signal indicative of the pressure within the ascending aorta, or near the aortic arch, and a third signal from the thermistor indicative of temperature of the blood flowing in the ascending aorta or flowing from the heart to the ascending aorta. The processor then calculates a pump flow output based on the first signal and second signal, calculates total cardiac output based on the third signal, and calculates native cardiac output of the beating heart based on the pump flow output and total cardiac output by subtracting the pump flow output from the total cardiac output. The third signal is then used to determine clinically relevant variables including global end-diastolic volume (GEDV), the intrathoracic blood volume (ITBV), the intrathoracic thermal volume (ITTV), pulmonary thermal volume (PTV), extravascular lung water (EVLW), cardiac index, global ejection fraction, and stroke volume.

In one aspect, a system is provided for measuring performance of a beating heart which includes an intracardiac blood pump with a tubular cannula that has proximal and distal openings and a cylindrical surface disposed between the proximal and distal openings. The tubular cannula is configured to be positioned in the aorta. The intracardiac blood pump also includes an electrically driven motor, a rotor positioned within the blood pump (for example in the cannula), and an electrical line configured to supply current to the motor. In some embodiments the motor is implanted with the rotor. Optionally, the pump may be powered by an external motor with a drive cable that extends through the catheter and out to a drive unit located external to the patient.

The system may also include a catheter and a repositioning sheath. A thermistor is included, along with a source of fluid configured to provide a bolus of fluid into the blood stream going into or away from the heart. One or more additional sensors is used, including a sensor for measuring changes in motor current and blood pressure, and a processor. The catheter has proximal and distal end regions, with the distal end region connected to the cannula. The repositioning sheath is disposed about the catheter, and the thermistor is disposed in the distal end region of the catheter where it is configured to detect blood temperature flowing in the heart's aorta. The bolus of fluid changes blood temperature in vasculature flowing into or away from the beating heart. A first sensor detects changes in the motor current during operation, and a second sensor detects the blood pressure within the ascending aorta. The processor is configured to receive a first signal from the first sensor indicative of a change in the motor current, a second signal from the second sensor indicative of the blood pressure within the ascending aorta, and a third signal from the thermistor indicative of a temperature of blood flowing in the heart's ascending aorta. The processor is further configured to calculate a pump flow output based on the first signal and the second signal, calculate a total cardiac output based on the third signal, and calculate a native cardiac output of the beating heart based on the pump flow output and the total cardiac output.

In some implementations, the third signal indicates a change in temperature of blood flowing into the heart caused by the bolus of fluid. In some implementations, the third signal indicates a change in temperature of blood flowing near or through the proximal opening of the cannula. In some implementations, the processor is configured to determine the total cardiac output by detecting changes in the third signal as a function of time. In some implementations, the native cardiac output is calculated by subtracting the pump flow output from the total cardiac output. In some implementations, the thermistor is disposed in the proximal end region of the catheter. In some implementations, they system further comprises a second thermistor disposed on the catheter, the second thermistor configured to detect blood temperature near the catheter.

In some implementations, the processor is further configured to calculate from the first, second, and third signals at least one of global end-diagnostic volume, an intrathoracic blood volume, an intrathoracic thermal volume, a pulmonary thermal volume, a cardiac index, a stroke volume, an extravascular lung water, a cardiac power output, and a global ejection fraction. In some implementations, the processor is further configured to display the native cardiac output on a screen. In some implementations, the processor is further configured to record and store the native cardiac output and to display a history of the native cardiac output as a function of time.

In another aspect, a method is provided for determining native cardiac output of a heart. The method includes positioning by a catheter a repositioning sheath and an intravascular blood pump in a patient's aorta and driving the intravascular blood pump with a motor current to cause a motor inside the pump to pump blood from the left ventricle and into the patient's ascending aorta. The method also includes detecting a change in temperature of blood being pumped from the left ventricle into the ascending aorta, detecting a change in the motor current during pumping, detecting a pressure within the ascending aorta, calculating by a processor a total cardiac output based on the detected temperature change, calculating by the processor a pump flow output based on the detected change in motor current and the detected pressure, and subtracting by the processor the pump flow output from the total cardiac output to determine the native cardiac output.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Following below are more detailed descriptions of various concepts related to inventive methods and systems for measuring total cardiac output, mechanical cardiac output, and native cardiac output using a thermistor imbedded in an intravascular blood pump, for example in the catheter sheath associated with the mechanical support device. These calculations can be made simultaneously while the heart is beating to allow the determination of the native cardiac output of that heart. It should be appreciated that various concepts introduced above and discussed in greater detail below may be implemented in any number of ways, as the disclosed concepts are not limited to any particular manner of implementations. Examples of implementations and applications are provided solely for illustrative purposes and are not limiting.

The methods and systems described herein enable measurement of the total cardiac output, mechanical cardiac output, and native cardiac output using a thermistor imbedded in a catheter sheath of an intravascular blood pump based on a thermodilution technique. The measurement of the native cardiac output may be made while continuing to provide full mechanical support to the heart with the intravascular blood pump. The native cardiac output, as well as other variables derived from the measurements, may be displayed to a physician or pump operator in order to provide information related to the status and condition of the heart.

Figure 1A:
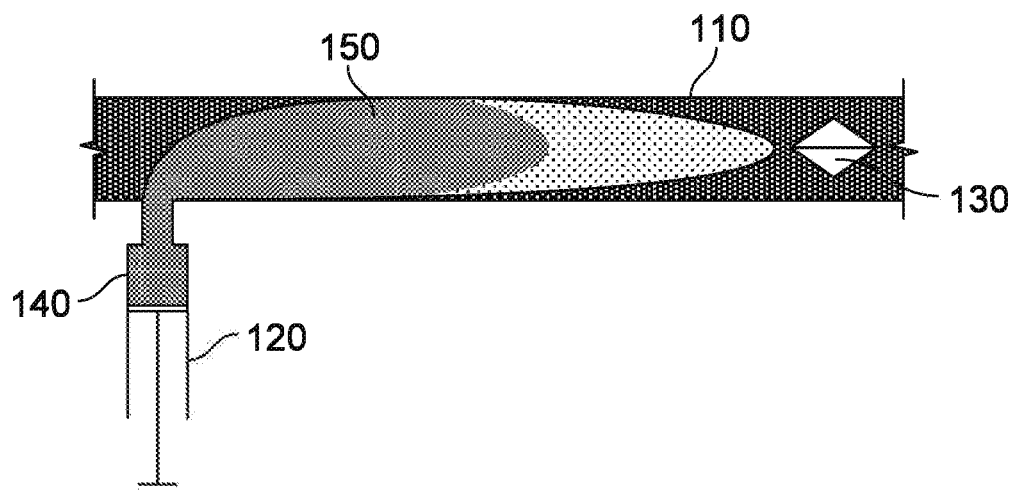
FIG. 1A illustrates a standard thermodilution technique to measure total cardiac output of a beating heart, according to an embodiment.

FIG. 1A is an illustration of a thermodilution technique used to measure cardiac output from a patient by detecting the temperature change in the patient's blood after application of a thermal source. The illustration includes the pulmonary artery 110, an intraluminal device 120, a temperature sensor 130, a fluid reservoir 140, and a fluid bolus 150. In this technique a clinician gains access to the pulmonary artery 110 of the patient using an intraluminal device 120. In certain implementations, the intraluminal device 120 is a syringe. A temperature sensor 130 is inserted into the pulmonary artery 110 using a right heart catheter such as a Swan-Ganz catheter. Such a catheter gains access to the pulmonary artery 110 from a site different to that used by the intraluminal device 120. The temperature sensor 130 is positioned in the vasculature in the direction of blood flow from the point of access of the intraluminal device 120. A cold fluid bolus 150 is then introduced into the superior vena cava 110 using the intraluminal device 120. The precise fluid bolus 150 is introduced into the pulmonary artery 110 from the fluid reservoir 140 contained in a syringe. The fluid bolus 150 should be at a different temperature than the physiological blood temperature. In some implementations, the fluid bolus 150 is of a temperature that is below that of the patient's blood, i.e. the fluid is cold. In some implementations, the fluid bolus 150 has a temperature of about 4° C. In some implementations, the fluid bolus 150 is a saline solution. In some implementations, the fluid bolus 150 includes a physiologically compatible fluid, such as a 5% glucose solution. In traditional thermodilution methods in which a fluid bolus is injected into the superior or inferior vena cava and the thermistor is in the pulmonary artery, the cold fluid traverses only the right atrium and the right ventricle. Furthermore, the traditional thermodilution method requires accessing the right heart of a patient.

Figure 1B:
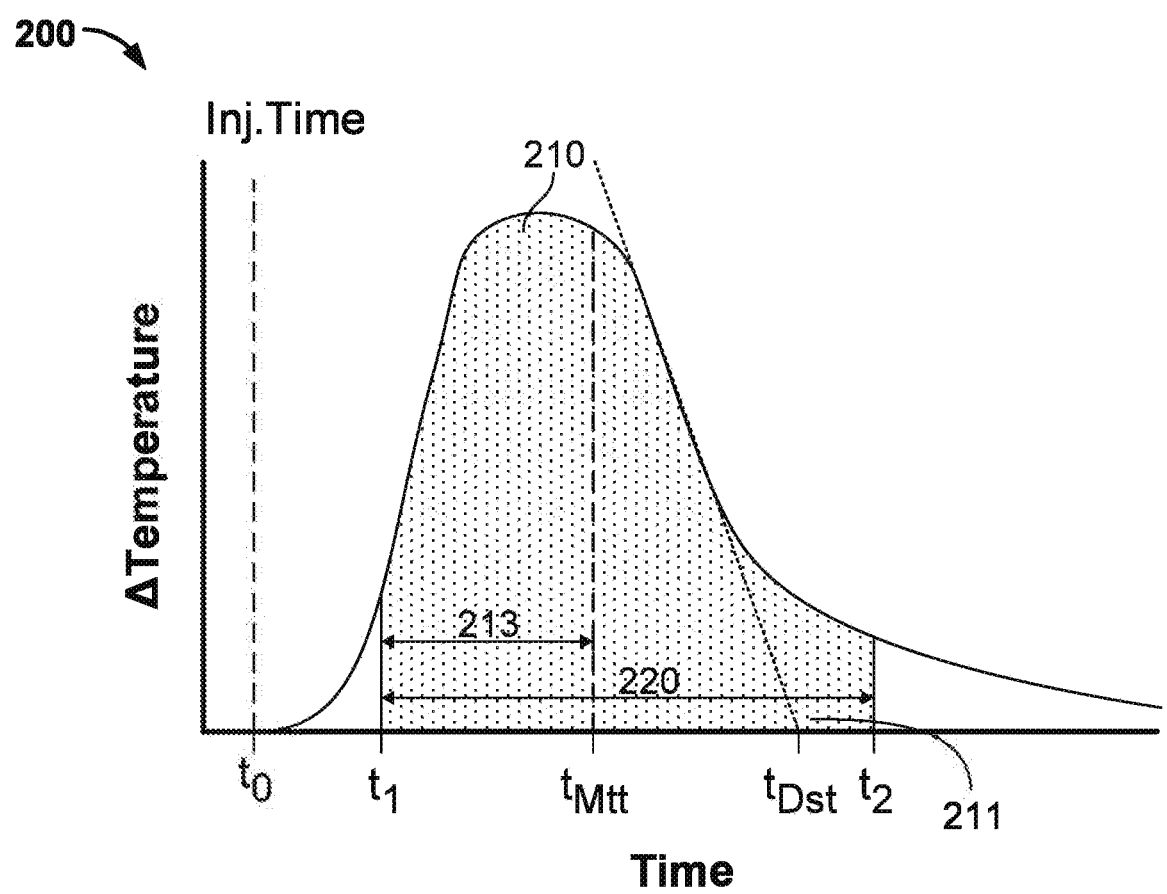
FIG. 1B illustrates a curve showing the variation in temperature $\Delta T$ of the blood within the artery.

FIG. 1B illustrates plot 200 displaying a thermodilution curve 210 showing the variation in temperature ΔT of the blood within the pulmonary artery 110 of the patient as detected by the temperature sensor 130. The fluid bolus 150 is introduced at time $t\_0$ and the change in temperature peaks and starts to reduce and tail off indicative of the amount of time it takes for the cold injected fluid to flow through the thermistor. The total cardiac output is determined by calculating the area under the curve 210 over a predetermined time period 220, such as between time $t\_1$ and time $t\_2$ in FIG. 1B, using well-established algorithms and mathematical techniques. Additional variables may be extracted from the thermodilution curve, including the mean transit time (MTt) 213 and downslope time (DSt) 211. The MTt 213 represents the time that it takes for half of the fluid bolus 150 to transit past the thermistor, while the DSt 211 is calculated from the exponential downslope of the thermodilution curve. The MTt 213 and DSt 211, in conjunction with the thermodilution curve, total cardiac output and other measurements, can be used to calculate a variety of clinically relevant variables.

A drawback of using traditional thermodilution techniques, as shown in FIG. 1A, to determine the total cardiac output is that the technique requires placement of the thermistor and Swan-Ganz catheter across the right heart and into the pulmonary artery (e.g., access to the pulmonary artery 110 by the intraluminal device 120, and access to the pulmonary artery 110 by the temperature sensor 130 using a catheter from a different access site in FIG. 1A). Such multiple access sites around the heart can increase the risk of vascular complications as well as infections. Additionally, placement of the catheter in the pulmonary artery is sometimes challenging, has risk of vascular injury and arrhythmias, and requires the use of X-rays to confirm that it is in a correct location every time the catheter is moved.

Figure 2:
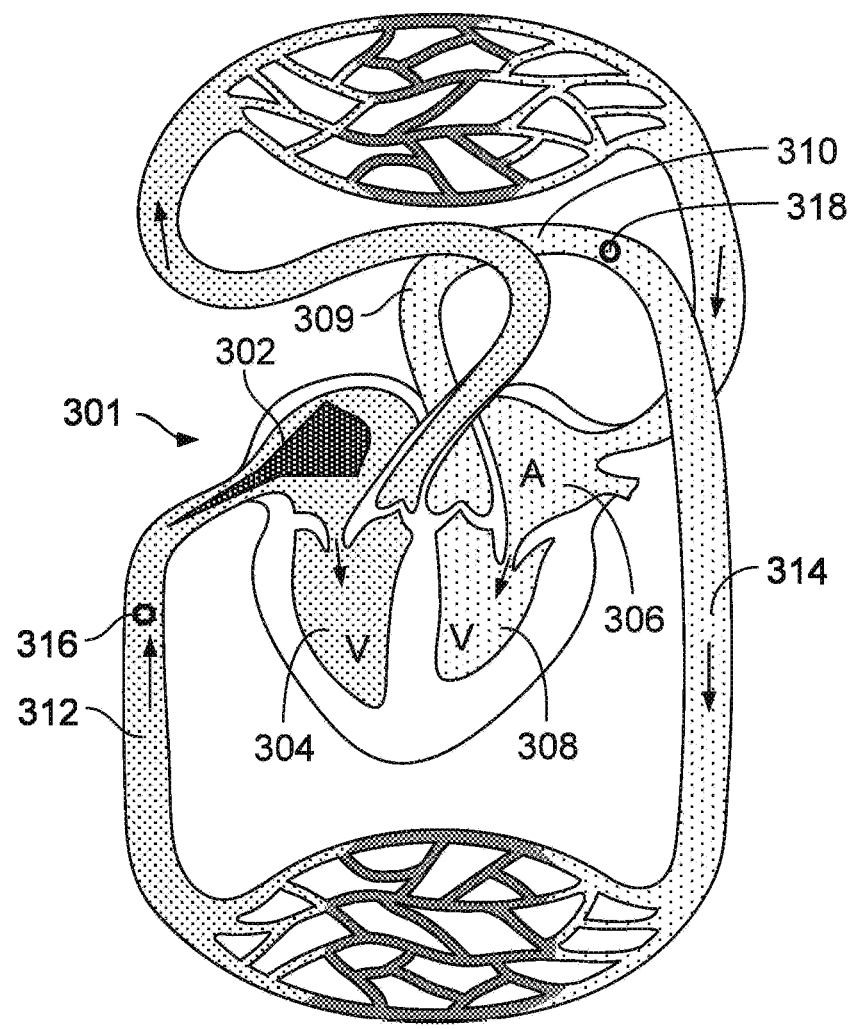
FIG. 2 illustrates a transpulmonary thermodilution technique to measure total cardiac output of a beating heart, according to an embodiment.

FIG. 2 illustrates a transpulmonary thermodilution technique to measure total cardiac output of a beating heart 301 according to an embodiment. The illustration includes a heart 301 including a right atrium 302, a right ventricle 304, a left atrium 306, a left ventricle 308, an aorta 309, and an aortic arch 310. The illustration also includes aspects of the pulmonary circuit including a peripheral vein 312, and peripheral artery 314. The blood flows from the left atrium 306 to the left ventricle 308, into the aorta 309, and over the aortic arch 310 into the body. Blood returns to the heart 301 through the right atrium 302 and right ventricle 304. In a transpulmonary thermodilution technique, a cold fluid bolus is injected into the peripheral vein 312 at point 316. The blood traverses the pulmonary circulation and the temperature of the blood is measured by a thermistor (not shown) positioned in the aorta 309 at point 318. The injection of the cold fluid bolus into the peripheral vein eliminates the need for any additional right catheter placement into the heart for the fluid injection. Using the peripheral vein for the injection of the fluid bolus presents less risk to the patient than placement of additional catheters, such as Swan-Ganz catheters, into the heart. In some implementations, the fluid bolus is injected into the inferior vena cava. In some implementations, the thermistor is positioned near the aortic valve.

Total cardiac output is calculated from the measured temperature change. The temperature measured by the thermistor at point 318 is recorded over time as a thermodilution response curve. The total cardiac output may be calculated from the recorded temperatures measurements based on the area under the curve showing the change in measured temperature over time, as depicted in FIG. 1B. The total cardiac output is equivalent to the sum of the native cardiac output and the output of the cardiac assistance device. Determination of the native cardiac output using thermodilution allows instantaneous determination of the native cardiac output while the pump is operating. The native cardiac output can be used to aid medical professionals in making decisions regarding the use of the cardiac assistance device.

Additionally, measuring the mean transit time (MTt) and downslope time (DSt) of the area under the ΔT v. time curve (see, for example, FIG. 1B) allows for the calculation of additional clinically relevant variables. The variation of temperature over time measured by the thermistor and recorded in the thermodilution curve may also be used to calculate the global end-diastolic volume (GEDV), the intrathoracic blood volume (ITBV), the intrathoracic thermal volume (ITTV), pulmonary thermal volume (PTV), extravascular lung water (EVLW), cardiac index, global ejection fraction, and stroke volume. These variables may provide physicians or operators with additional information about the performance of the heart and the degree of pulmonary congestion which may guide treatment decisions.

The PTV can be calculated by multiplying the total cardiac output by the DSt. The PTV is representative of the distribution of the cold fluid volume in pulmonary circulation. The ITTV is calculated from the total cardiac output multiplied by the MTt. The ITTV is representative of the distribution of the cold fluid volume. The GEDV is representative of the volume of blood contained in all four chambers of the heart and is an index of cardiac preload, and is calculated by subtracting the PTV from the ITTV. This can be expressed alternatively by GEDV=total cardiac output× (MTt−DSt). GEDV can be used to clinically assess patient response to volume loading and allows a physician to more accurately evaluate cardiac preload. The ITBV is representative of the volume of blood in the heart and in pulmonary circulation and can be used to inform clinicians on volume status of the heart and cardiac performance. The ITBV can be calculated by multiplying the GEDV by 1.25, or alternatively, by multiplying 1.25×CO (total cardiac output)× (MTt−DSt). The EVLW is calculated from the ITBV and ITTV. The EVLW is a volumetric measure of the amount of water in the pleural space. The EVLW is calculated by subtracting the ITBV from the ITTV. EVLW can be used to measure lung congestion, which is commonly associated with left ventricular failure after an acute myocardial infarct. The cardiac index is an overall measure of cardiac performance calculated with the formula CI=CO/BSA, where CI is the cardiac index, CO is the cardiac output, and BSA is the body surface area. Clinically relevant information may be obtained from the calculation of the cardiac index using either of the total cardiac output or the native cardiac output. Stroke volume is an index of left ventricular function which uses the formula SV=CO/HR, where SV is the stroke volume, CO is the cardiac output, and HR is the heart rate. Cardiac power output is a measure of the heart function in Watts calculated using the equation CPO=mAoP*CO/451, where CPO is the cardiac power output, mAoP is the mean aortic pressure, CO is the cardiac output, and 451 is a constant used to convert mmHG×L/min into Watts. Additional variables can be calculated from the thermodilution measurements according to the equation:

$$Q = K(T_b - T_i)(V_i - V_d)\frac{60}{AUC}$$

Wherein Q is the flow, $T_b$ is the initial temperature in the femoral artery, $T_i$ is the temperature of the injected fluid, K is a constant accounting for specific heat of blood and fluid taking into account the density of chosen fluid and blood (K being equivalent to 1.1021 when saline is used), $V_i$ is the injected volume, $V_d$ is the dead space volume in the catheter through which the fluid is injected into the body, and AUC is the area under the thermodilution curve in ° C.·s. Any of the preceding cardiac variables can be quickly calculated using the measurements obtained by the thermistor and percutaneous pump.

Figure 3:
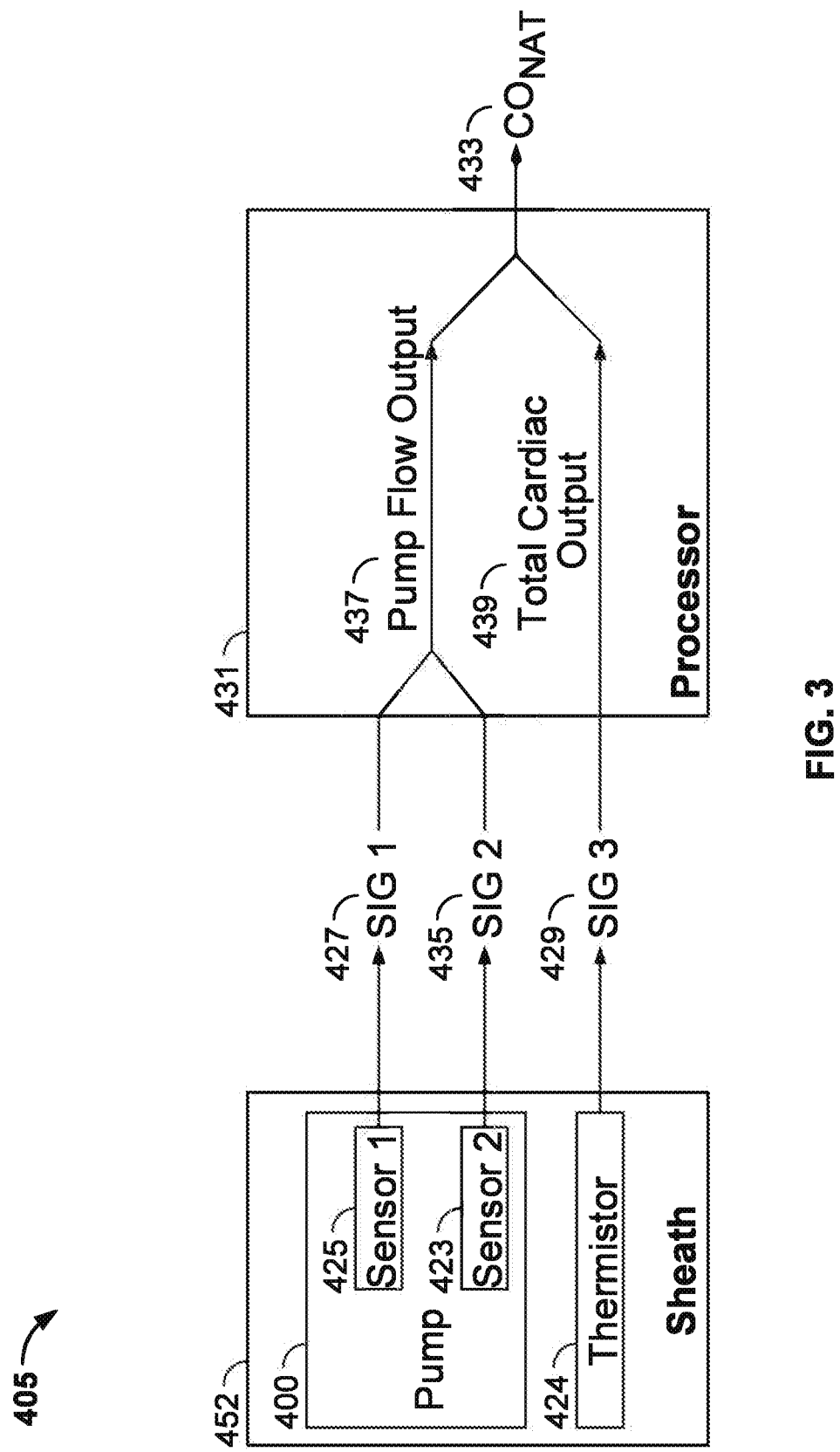
FIG. 3 illustrates a block diagram of a method of determining the native cardiac output of a beating heart using a signal generated by a thermodilution technique used with a heart pump placed in a beating heart, according to an embodiment.

FIG. 3 illustrates a block diagram 405 showing a transpulmonary thermodilution system that can be used to determine the native cardiac output of a beating heart. The system uses signals measured by a cardiac assistance device and imbedded temperature sensor. The system includes a pump 400 and a thermistor 424 contained in a sheath 452, a first sensor 425, a second sensor 423, a first signal (SIG 1) 427, a second signal (SIG 2) 435, a third signal (SIG 3) 429, a processor 431, and an output variable ($CO_{NAT}$) 433. The pump 400 and the thermistor 424 are delivered to a position in the heart and the aorta through a sheath 452. The pump 400 includes a first sensor 425 which outputs a first signal 427 to the processor 431, and a second sensor 423 which outputs a second signal 435 to the processor 431. The first sensor 425 may be a motor current sensor, and may output a first signal 427 of the electrical current drawn by the pump motor to the processor 431. The second sensor 423 may be a pressure sensor which outputs a second signal 435 of the pressure in the aorta to the processor 431. The thermistor 424 is placed in the sheath 452 near the proximal end of the pump 400, and measures the change in temperature in the blood surrounding the pump and thermistor and outputs a third signal 429 to the processor 431 indicative of the temperature change in the blood at the location of the thermistor. In embodiments, a bolus of cold saline is introduced into the vasculature, though other fluids may also be used. The temperature change measured by the thermistor 424 arises from the saline bolus as it flows within the vasculature, which changes the temperature of the blood flowing into or away from the heart. The first signal 427 and the second signal 435 are collected at the processor 431 and are used to calculate a pump flow output 437. The third signal 429, from the thermistor 424, is collected at the processor 431 and used to calculate a total cardiac output 439 while the heart is beating or unarrested. The pump flow output 437 is subtracted from the total cardiac output 439 in order to determine the native cardiac output 433, representative of a cardiac state while the heart is beating, for example the native cardiac output ($CO_{NAT}$).

In some implementations, the pump 400 is any suitable pulmonary assistance device. In some implementations, the pump 400 is an intracardiac blood pump. The pump 400 includes a motor which pulls blood through the pump 400 providing support to the heart's pumping function. The pump 400 is connected by a catheter to an external controller or processor 431. The pump 400 is delivered through a sheath 452 to a desired position in the heart, for example across the aortic valve. In some implementations, the first signal 427 includes both the pressure measurement at the second sensor 423 on the pump 400 and a motor current from the first sensor 425. In some implementations, the processor 431 includes a lookup table used to determine the pump flow output 437 based on the motor current reported by the first signal 427 and the pressure reported by the second signal 435.

The fluid bolus changes the temperature of the blood, because the fluid bolus injected into the vasculature is colder than the temperature of the blood. The thermistor 424 may detect a change in blood temperature as the bolus reaches and passes the thermistor 424. The total cardiac output can be calculated as described in relation to FIG. 1B.

Figure 4:
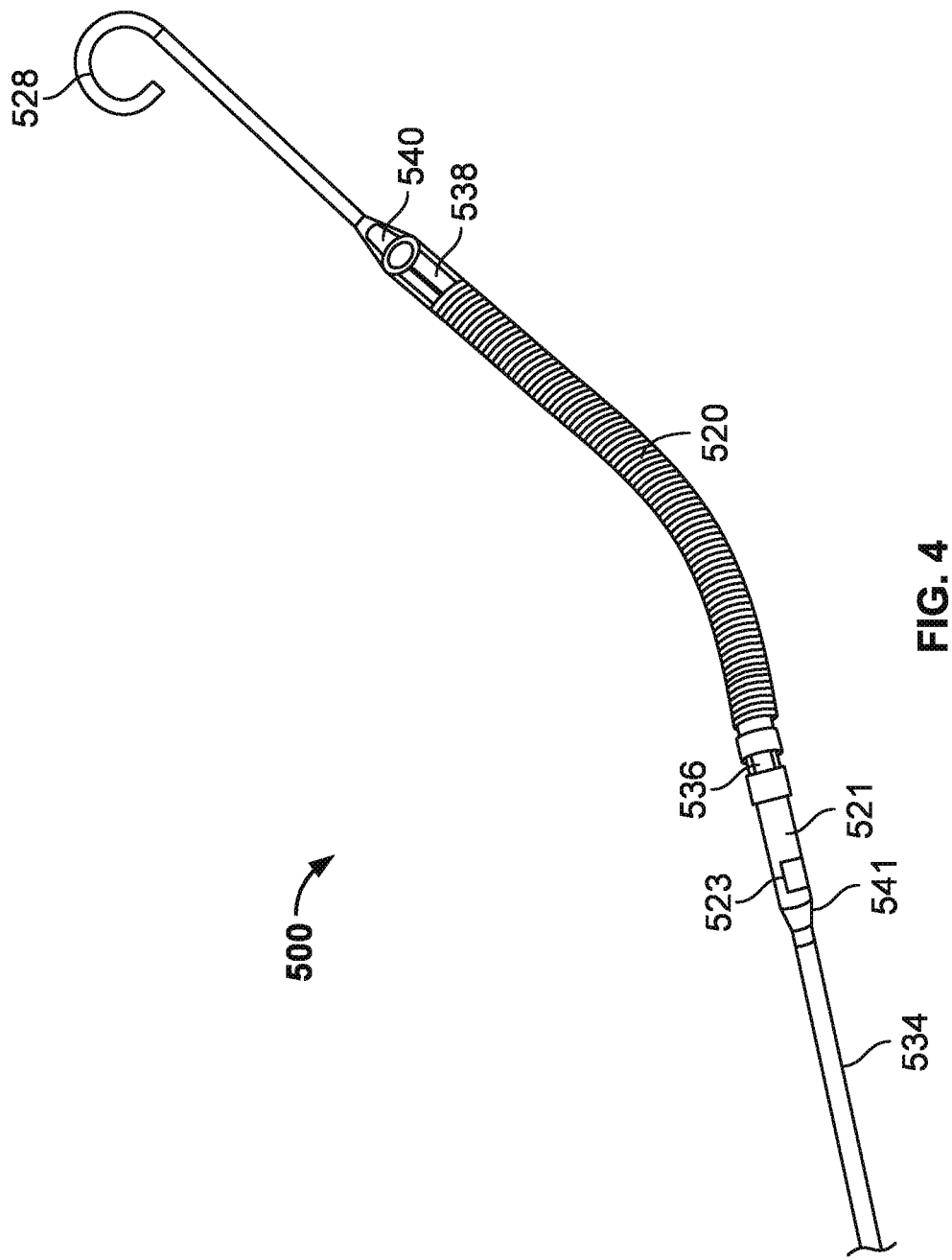
FIG. 4 shows a perspective view of percutaneous pump according to an embodiment.

FIG. 4 shows a perspective view of a percutaneous pump 500 configured to measure blood temperature during use of the pump within the heart. The percutaneous pump 500 includes a cannula 520, a pump housing 521, a catheter 534, a distal end 540, a proximal end 541, a distal projection 528, an inflow aperture 538, an outflow aperture 536, and a sensor 523. The catheter 534 is coupled to the pump housing 521 at the proximal end 541 of the percutaneous pump 500. In some implementations, the percutaneous pump 500 includes a motor. In such cases, the catheter 534 may house electrical lines coupling the pump motor to one or more electrical controllers or sensors. In certain implementations, the percutaneous pump 500 is driven by a pump with a motor located external to the patient (and connected to the pump by a flexible drive shaft). The catheter 534 may also house other components, such as a purge fluid conduit, a guidewire conduit, or other conduits. The pump housing 521 includes one or more outflow apertures 536 configured to expel or exhaust blood drawn into cannula 520 out of the percutaneous pump 500. In some implementations, percutaneous pump 500 includes one or more sensors positioned on the cannula 520, the pump housing 521, or the catheter 534. For example, one or more pressure sensors 523 may be positioned on the percutaneous pump 500 to sense changes in pressure within the heart. The pressure sensor 523 sends a signal indicative of a pressure measurement within the heart to the processor (not shown). Pressure measurements may be used by the processor along with motor current measurements obtained from motor current information to understand the cardiac assist device output, or the cardiac assistance being provided by the percutaneous pump 500 to the heart.

Figure 5:
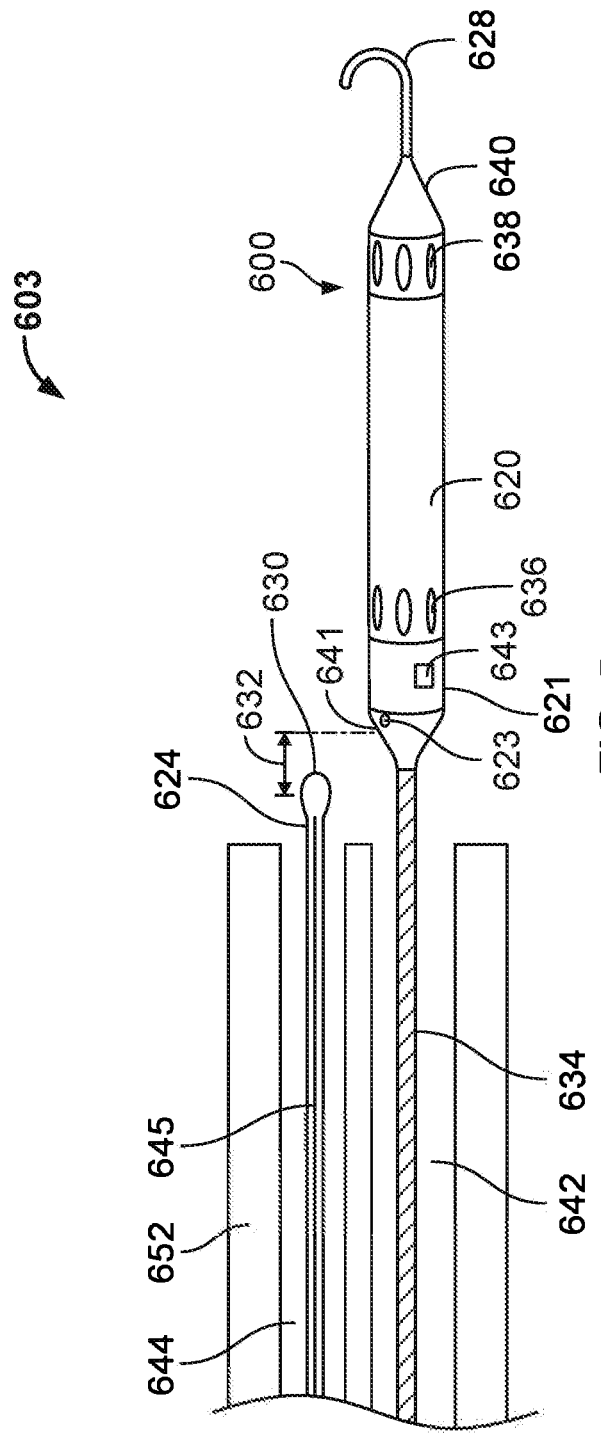
FIG. 5 shows a perspective view of a transpulmonary thermodilution (TPTD) assembly comprising a percutaneous pump and a thermistor inserted into a dual lumen sheath during manufacture, according to an embodiment.

FIG. 5 shows a perspective view of a transpulmonary thermodilution (TPTD) assembly 603 comprising a percutaneous pump 600 (e.g., the percutaneous pump 500 of FIG. 4, or any suitable percutaneous pump) and a first thermistor 624 inserted into a sheath 652. The percutaneous pump 600 includes a cannula 620, a pump housing 621, a catheter 634, a distal end 640, a proximal end 641, a distal projection 628, an inflow aperture 638, an outflow aperture 636, and a sensor 623. The first thermistor 624 includes a temperature sensitive head 630. A second thermistor 634 is positioned on the cannula 620. The percutaneous pump 600 and the first thermistor 624 are delivered to a patient's heart using a repositionable sheath 652. The sheath 652 includes a first lumen 642 sized for delivery of the percutaneous pump 600, and a second lumen 644 sized for delivery of the first thermistor 624. In some implementations, the percutaneous pump 600 may be preloaded in the sheath 652 during manufacture. As illustrated, the sheath 652 may be a dual lumen sheath for delivery of the percutaneous pump 600 and first thermistor 624 to the heart. A dual lumen sheath is described in greater detail in co-pending U.S. patent application Ser. No. 14/827,741 title "Dual Lumen Sheath for Arterial Access," the contents of which are herein incorporated by reference.

The first thermistor 624 is delivered to the heart through the sheath 652, such that the first thermistor 624 is positioned proximal to the proximal end 641 of the percutaneous pump 600. In this position, the first thermistor 624 can access the vasculature via the same sheath as the percutaneous pump 600, such that the first thermistor 624 is placed without requiring additional access to the vasculature. Positioning the temperature sensitive head 630 of the first thermistor 624 near the percutaneous pump 600 allows the first thermistor 624 to detect changes in temperature of the blood flowing through the aorta and the blood exiting the percutaneous pump 600 at the outflow apertures 636. While the first thermistor 624 is depicted in a position proximal to the proximal end 641 of the percutaneous pump 600, it will be apparent to one of skill that the first thermistor 624 may be positioned elsewhere in the vasculature, including in the aortic arch or the femoral artery.

As shown, in some embodiments a second thermistor 643 can be added to the percutaneous pump 600 to derive temperature changes in two locations in the heart and the aorta. In some implementations, the presence of a second thermistor 643 enables more accurate readings and more accurate cardiac output measurements than a pump having a single first thermistor 624. For example, the first thermistor 624 is depicted in the sheath 652, but may alternatively be imbedded in the sheath 652 or in the catheter 634 of the percutaneous pump 600. Similarly, the first thermistor 624 can be positioned in the sheath and the second thermistor 643 can be positioned on the catheter. For example, the second thermistor 643 can be positioned proximal to the outflow apertures 636 to accurately detect the fluid temperature of the blood exiting through the outlet apertures 636. In some implementations, the sheath 652 is a single lumen sheath. In some implementations, the first thermistor 624 is placed in the femoral artery rather than in the ascending aorta. One of skill in the art will realize that the percutaneous pump 600 can be designed to include a single thermistor, or multiple thermistors.

In some implementations the first thermistor 624 is not delivered through a second lumen 644, but is rather imbedded in the sheath 652 or in the catheter 634 of the percutaneous pump 600. A thermistor which is imbedded in the sheath 652 or catheter 634 as part of the assembly, rather than loaded through the second lumen 644 requires less set up and as a result placement of the assembly may be easier and less time consuming.

In some implementations, the temperature sensitive head 630 of the thermistor 624 is formed from a semiconducting material such as a sintered metal oxide encapsulated in an epoxy or glass. The thermistor 624 includes a catheter 645 connecting the thermistor 624 through the sheath 652 to a processor located outside of the patient's body (not shown). The processor records the temperature of the blood sensed by the temperature sensitive head 630 of the thermistor 624. A physician or operator may inject a bolus of saline or other fluid, into the patient's vasculature, thereby changing the temperature of the blood. The thermistor 624 measures the temperature of the blood as it flows through the heart/aorta and the measurements can be used in order to determine the total cardiac output using the thermistor 624. The thermistor 624 positioned on or near the percutaneous pump 600 can be used to determine the total cardiac output while the percutaneous pump 600 delivers continuous mechanical support to the heart.

In one example, a bolus of cold saline solution is introduced into a patient's vasculature, for example at the femoral vein. The temperature of the blood flowing past the thermistor 624 is then monitored, and the change in temperature over time is measured and used to extract variables including the total cardiac output and other variables representing cardiac function. These clinically relevant variables can be provided to physicians and operators without stopping the percutaneous pump support, providing a real-time assessment of native cardiac output while mechanical circulatory support is active. In this way, hemodynamic support can be maintained while critical information about cardiac output is obtained. Additionally, the response to the pump flow can be instantaneously evaluated without moving the patient. The variables calculated from the measurements of the thermistor and other sensors can be presented to the physician or operator to enable them to make decisions about the care of the patient and how much cardiac assistance is needed. Based on the variables extracted from the thermistor 624 temperature measurements and information from other sensors, including motor current sensors and pressure sensors on the percutaneous pump, the native cardiac output can be determined.

The temperature changes over time measured by the thermistor 624, as well as measurements from other sensors on the percutaneous pump 600, are received by the processor as input signals. The processor includes software and/or firmware including programming to allow the processor to receive and record the input signals and convert them to variables that can be used to calculate the native cardiac output and/or other relevant variables. The native cardiac output is determined by the equation:

$$CO_N = CO_{TOT} - CD_{Flow}$$

Where $CO_N$ is the native cardiac output of the heart itself, $CO_{TOT}$ is the total cardiac output derived from the temperature measurements of the thermistor, and $CD_{flow}$ is the flow of the cardiac device or percutaneous pump calculated from the motor current drawn by the pump motor and pressure. Based on the calculated native cardiac output and other variables that can be calculated by the processor, the physician or operator may determine that a patient should be weaned off of the cardiac assistance device or that increased support is required. The use of the thermistor to provide these variables to physicians and clinicians increases patient safety during the weaning process.

Figure 6:
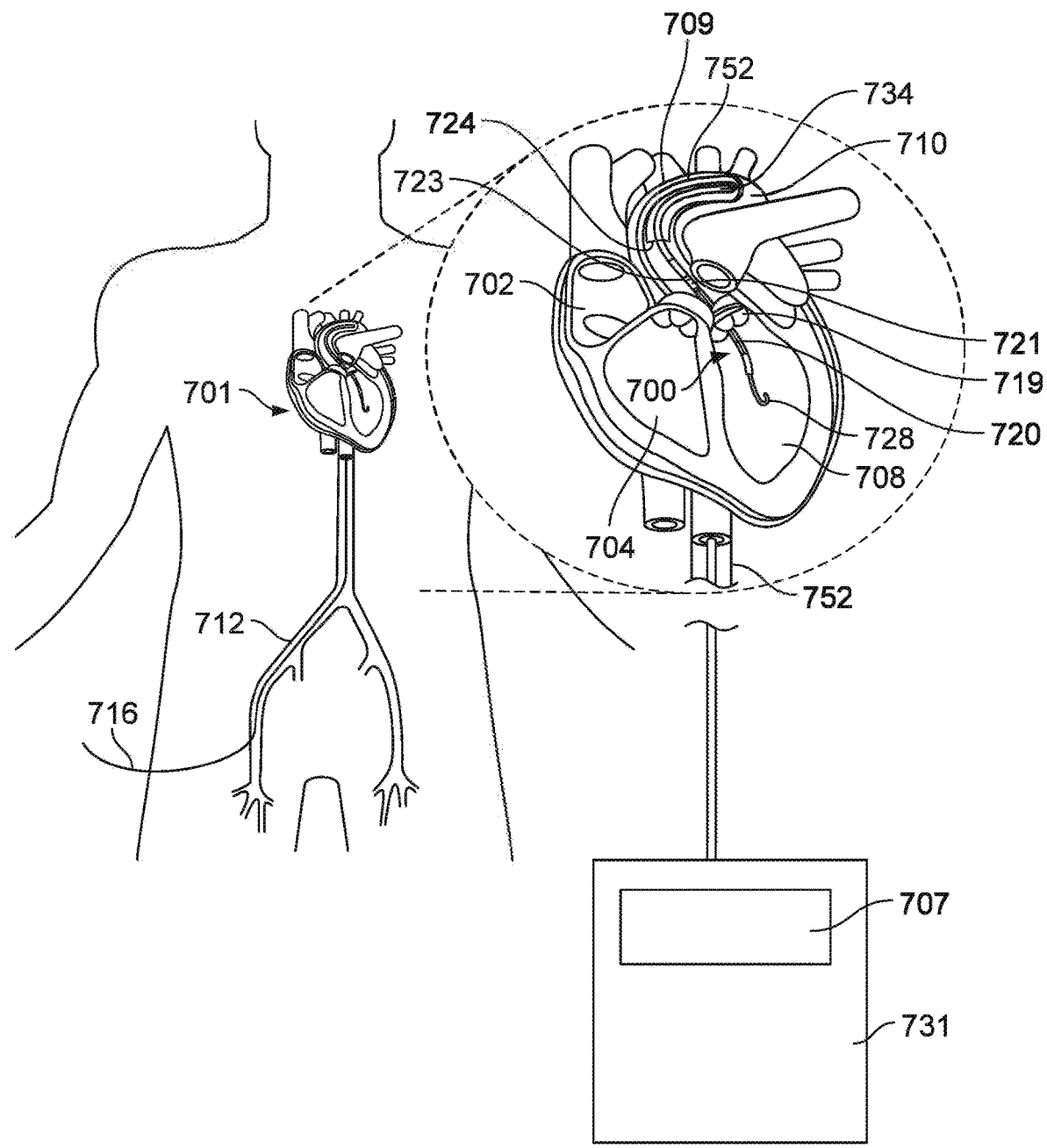
FIG. 6 illustrates placement of the TPTD assembly of FIG. 5 in the ascending aorta of a patient with a beating heart, according to an embodiment.

FIG. 6 illustrates placement of the TPTD assembly 603 of FIG. 5 in the ascending aorta 710 of a beating heart 701. The heart 701 includes a right atrium 702, a right ventricle 704, a left ventricle 708, and aspects of the pulmonary circuit including an aortic arch 709, an aorta 710, and an aortic valve 719 are also included. The aorta 710 is connected to the femoral artery 712. A percutaneous pump 700 is situated within the heart 701. The percutaneous pump 700 includes a sheath 752, a cannula 720, a pump housing 721, a catheter 734, a pressure sensor 723, and a distal projection 728. The percutaneous pump 700 extends across the aortic valve 719, so that a distal portion of the cannula 720 of the percutaneous pump 700 is in the left ventricle 708 and a proximal portion of the cannula 720 of the percutaneous pump 700 is in the aorta 710. A thermistor 724 is located at the proximal end of the percutaneous pump 700 in the aorta 710, and may be imbedded in the sheath 752 or catheter 734. The pump 700 is coupled to a processor 731 located external of the patient, the processor 731 including a display screen 707. The pump housing 721 may house a motor (not shown) and impeller (not shown). The percutaneous pump 700 may be powered by an implantable motor disposed in the pump housing 721. The impeller and motor which draws blood from the left ventricle 708 into the cannula 720, through the cannula 720 across the aortic valve 719, and ejects the blood into the aorta 710. The percutaneous pump 700 also includes a pressure sensor 723 proximal to the pump housing. The percutaneous pump 700 may be placed by a guidewire or sheath, such as sheath 752. The sheath 752 may be a dual lumen sheath as illustrated in FIG. 5, or a single lumen sheath. The catheter 734 extends from the percutaneous pump 700 through the vasculature of a patient and out at an incision 716 in the femoral artery 712. In some implementations, the catheter 734 houses the drive shaft, purge lines, saline lines, or other lines or lumens which extend from outside a patient's body to the percutaneous pump 700.

Placing the thermistor 724 near the pump housing 721 at a proximal end of the percutaneous pump 700 allows for measurement of changes in temperature of blood moving through the heart. The signal from the thermistor 724 can be sent to the processor 731 to calculate the total cardiac output including both native heart cardiac output and the assistance of the percutaneous pump 700. Using flow estimates from measurements of the motor current supplied to the percutaneous pump 700 and pressure measurements from the pressure sensor 723, the native cardiac output and other variables indicative of cardiac performance may be quickly determined and supplied to the physician or operator of the device.

During use, physicians or device operators may monitor the functioning of the percutaneous pump 700 on a display screen 707 coupled to the processor 731. The display screen 707 may provide estimates of the flow rate through the percutaneous pump 700 based on an electrical current drawn from the motor. In order to provide additional information regarding pump and heart performance to physicians and operators, the thermistor 724 is positioned proximal of the pump housing 721 in a downstream direction of the saline bolus injection site. This positioning of the thermistor with regard to the percutaneous pump and the saline bolus injection provides a consistent and reliable temperature change measurement and thermodilution curve. The thermistor 724 may be imbedded in the catheter 734, in the sheath 752, or in the pump 700. The thermistor 724 is positioned to detect the temperature of blood flowing past the percutaneous pump 700 in the aorta 710. The positioning of the thermistor 724 enables measurement of the total cardiac output, or other key hemodynamic parameters, during operation of the percutaneous pump 700 using the transpulmonary thermodilution techniques. Simultaneously to the measurement of total cardiac output by the thermistor 724, the cardiac assistance provided by the percutaneous pump 700 may be measured using the motor current drawn by the pump motor and pressure measured in the heart to calculate the flow rate through the percutaneous pump 700. This information is useful to physicians or operators in making decisions about continued care for a patient. Determinations about whether to wean a patient off of a cardiac assist device or to increase the support provided by the device may benefit from the additional information about cardiac performance provided by the thermistor 724 used in conjunction with the percutaneous pump 700.

The thermistor 724 has a temperature sensitive tip which can be used as a sensor to measure the temperature of surrounding blood. In some implementations, the thermistor 724 is sized between about 38 and 42 gauge. In some implementations, the thermistor 724 is threaded through the catheter 734 of the percutaneous pump 700 after the pump has been placed in the heart 701. In some implementations, the temperature sensitive tip is placed proximal to the pump housing 721. In some implementations, the temperature sensitive tip is placed about 3 cm, 4 cm, 5 cm, 6 cm, or any other suitable distance from the pump housing 721. In some implementations, multiple temperature sensitive thermistors are placed in order to determine temperature changes in two locations in the heart and the aorta. Placement of the thermistor 724 proximal to the pump housing 721 in the ascending aorta 710 enables measurement of the total cardiac output. In some implementations, the thermistor 724 measures the temperature of the surrounding blood and reports the temperature to the processor 731 outside of the body which records the temperature as a function of time. In some implementations, the processor 731 calculates and records the native cardiac output at intervals in order to track the native heart performance.

The measurements from the thermistor 724 and percutaneous pump 700 may be displayed in real-time to physicians and clinicians on the display 707. Additionally, historical data may be recorded for an individual patient, allowing for the time-dependent measurements to be longitudinally compared and displayed. The information can allow physicians and clinicians to make decisions regarding adjustment of support from the cardiac assistance device, or weaning a patient from the cardiac assistance device. The interface or display 707 may also indicate if the patient has improved or declined over time, indicated by the increase or decrease of the native cardiac output. This information can be provided to physicians and clinicians without removing the heart from cardiac assistance devices.

Figure 7:
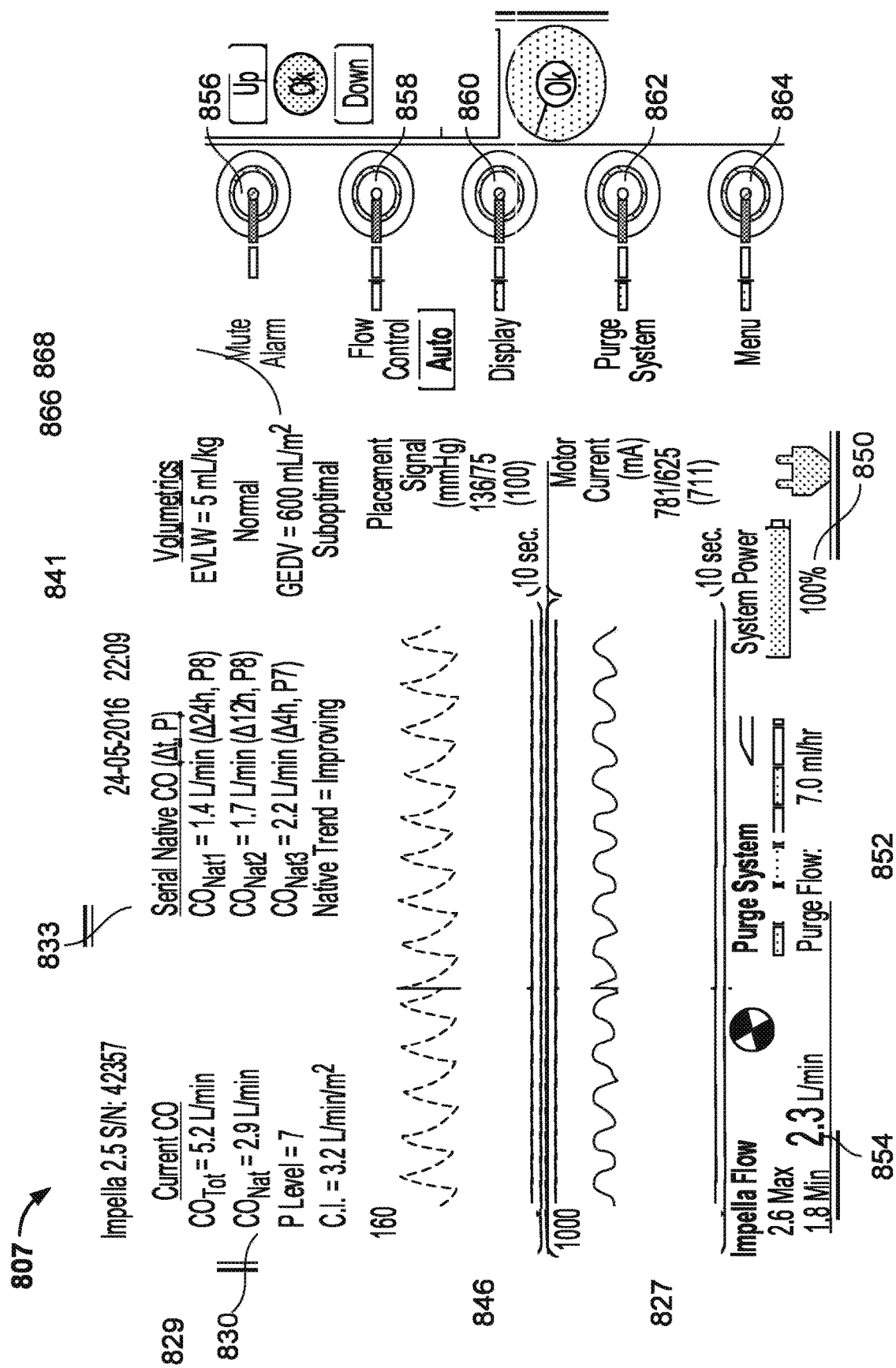
FIG. 7 shows an example controller displaying native cardiac output and other variables.

FIG. 7 shows an example controller screen 807 displaying total cardiac output and other cardiac variables. The example controller screen 807 displays a placement signal 846, a motor current signal 827, a total cardiac output 829, a native cardiac output 830, a serial native cardiac output 833, a native trend 841, an extravascular lung water measurement 866, a global end-diastolic volume measurement 868, a flow status indicator 854, a purge system indicator 852, a system power indicator 850, an alarm button 856, a flow control button 858, a display button 860, a purge system button 862, and a menu button 864.

The placement signal 846 displays a measurement of the blood pressure. The placement signal 846 displays the blood pressure over time, and the measurements displayed may be derived from a sensor on the intravascular pump (such as intravascular pump 500 in FIG. 4, intravascular pump 600 in FIG. 5, or intravascular pump 700 in FIG. 6) during operation of the pump. The placement signal 846 may be used by a physician to determine the positioning of the pump within the heart by monitoring the measured pressure to determine when the pump is in a correct placement within the heart. The motor current signal 827 displays a measurement of the electrical current drawn by the pump motor over time in units of mA. The motor current signal 827 may display measurements which are determined by a sensor on the pump motor within the pump, or within the processor or controller itself. The placement signal 846 and the motor current signal 827 can be used with the pressure measurement to calculate the flow rate of the intravascular pump by accessing a lookup table based on the motor current and pressure in the heart. The flow rate provides a measure of the mechanical assistance provided to the heart by the intravascular pump, or the pump flow output.

The total cardiac output 829 displays a measure of the total cardiac output from the heart's native beating and any mechanical assistance as measured by a thermodilution technique within the heart. The total cardiac output is measured by a thermistor which detects a change in the blood temperature in the heart in response to the injection of a saline bolus into the vasculature. Based on the detected change in blood temperature over time, the total cardiac output is calculated. The total cardiac output is displayed in L/min. The native cardiac output 830 can be calculated by subtracting the pump flow output from the total cardiac output 829. The native total output, displayed in L/min, provides an operator with information about the amount of output being produced by the heart itself. This can be useful in making therapeutic decisions, especially related to the weaning of a patient off of a cardiac assistance device such as the intravascular pump. The serial native cardia output 833 displays the calculated native cardiac output for several intervals, in order to provide an operator with historical data. The native trend 841 additionally provides the operator with a simple summary of the cardiac performance based on the historical data of the serial cardiac output 833. For example, on controller screen 807, the most recent native cardiac output ($CO_{NAT3}$) reported in the serial native cardiac output 833 list is greater than the previously recorded native cardiac outputs ($CO_{NAT2}$ and $CO_{NAT1}$), indicating that the heart currently has an increased native output. Therefore, the native trend 841 displays the status "Improving." In some implementations, the controller screen 807 includes more or less entries in the serial native cardiac output 833 display. In some implementations, additional recorded entries are accessed on an additional screen of the controller screen. Presenting the operator with the historical native cardiac output allows the operator to understand the trend of the patient's heart performance and health. This information can be useful in determining whether to increase or decrease cardiac support.

Additional cardiac measurements may be reported on the control screen 807 to provide operators with additional clinically relevant information. For, example, the extravascular lung water measurement 866 and the global end-diastolic volume measurement 868 are displayed on the control screen 807. The EVLW and GEDV can be calculated form the native cardiac output as discussed with regard to FIG. 2. Other hemodynamic measurements can be calculated from the placement signal 846, motor current signal 827, and total cardiac output 829 and can be reported on one or more screens of the control screen 807. The control screen 807 also includes a flow status indicator 854 which displays the current flow rate of the intravascular pump, as well as maximum and minimum flow rates achieved during a current operating session. The purge system indicator 852 displays a current status of the purge flow system, including the current flow rate of the purge fluid. The system power indicator 850 displays a charge status of an internal back-up battery, as well as whether the battery is charging and/or plugged in. The control screen 807 includes a series of buttons which allow an operator to access additional screens to control the pump and purge system, for example the purge system button 862 and the flow control button 858. The alarm button 856 can allow an operator to set or turn off an alarm, or may emit a sound or light when a measurement exceeds or falls below a preset limit. The display button 860 allows an operator to access an additional display screen, and the menu button 864 allows an operator to access a menu.

The control screen 807 may include additional or different displays of information, buttons, and status indicators. The control screen 807 is provided as a non-limiting example of a control screen used in conjunction with the system of FIG. 5 and FIG. 6.

Figure 8:
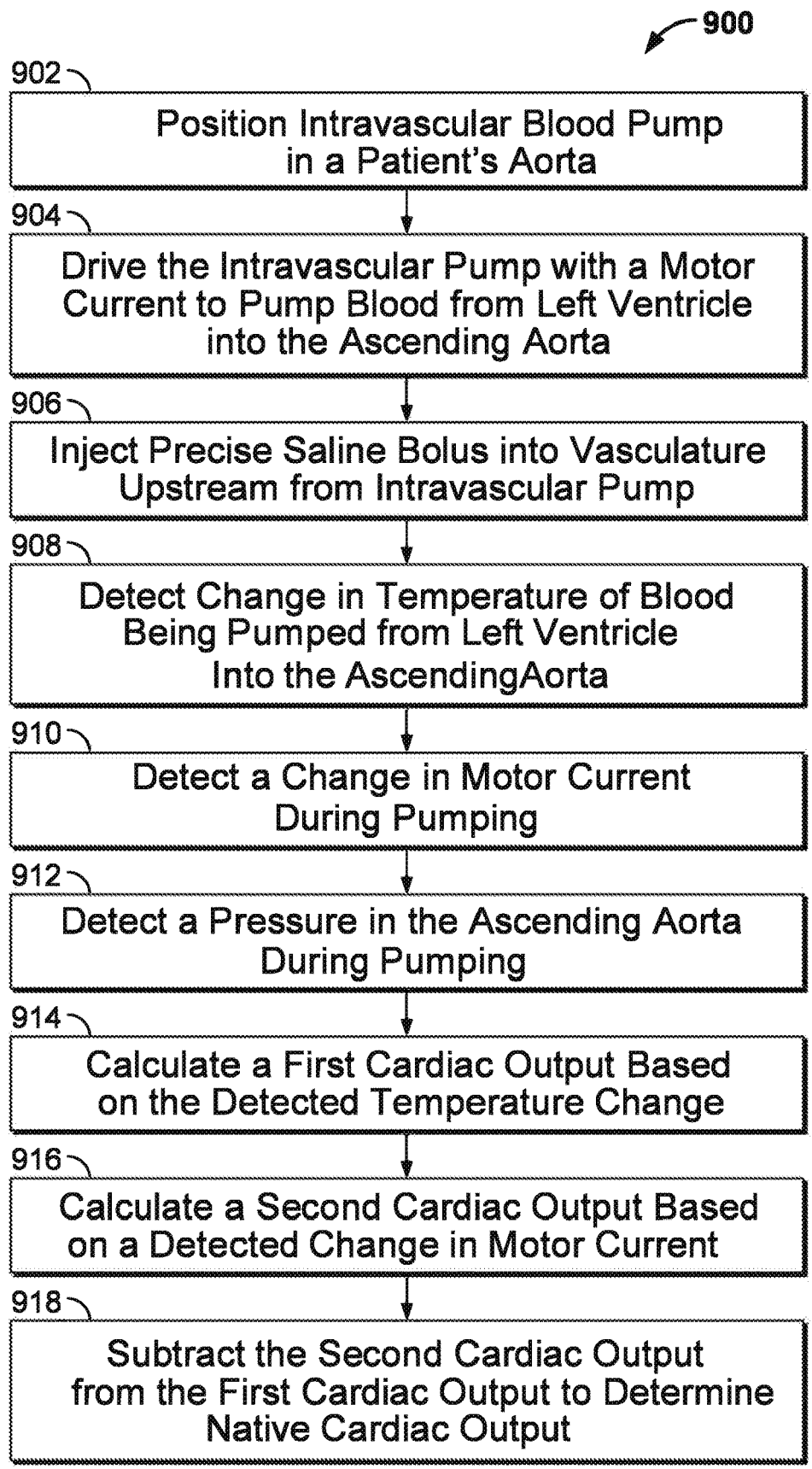
FIG. 8 shows a method for determining the native cardiac output using the setup of FIG. 5 according to an embodiment.

FIG. 8 shows a method 900 for determining the native cardiac output using the setup of FIG. 5 according to an exemplary embodiment. At step 902, the intravascular blood pump, such as the intravascular blood pump 500 in FIG. 4, intravascular blood pump 600 in FIG. 5, intravascular blood pump 700 in FIG. 6, or any other suitable intravascular blood pump, is positioned in the aorta (for example, as shown in FIG. 6). The intravascular blood pump can be delivered with the use of a guide wire and/or a repositionable catheter. The positioning of the intravascular blood pump can be monitored by the use of fluoroscopy, by monitoring the pressure surrounding the pump in the heart, or by any other suitable means. The intravascular blood pump is placed in the aorta such that the inflow apertures are positioned in the left ventricle, and the outflow apertures are positioned in the aorta. In some implementations, the intravascular blood pump is placed across the aortic valve.

At step 904, the intravascular blood pump is driven by a motor current to pump blood from the left ventricle in to the ascending aorta. The intravascular blood pump draws blood into the pump through the inflow apertures located in the left ventricle, and expels the blood through the outflow apertures into the ascending aorta in order to support the native cardiac function of the heart. The expelled blood is entrained in blood flowing through the aorta.

At step 906, a precise bolus of saline is injected into the vasculature in an upstream location from the location of the intravascular pump (e.g., in the femoral vein). The saline bolus is colder than the blood in the vasculature and causes a change in the temperature of the blood flowing through the vasculature to the left ventricle and into the aorta.

At step 908, the change in the temperature of the blood being pumped from the left ventricle into the ascending aorta is detected. The change in blood temperature is detected by a sensor or thermistor located at a proximal end of the intravascular pump. As the saline bolus passes through the vasculature and through the heart, the thermistor detects the temperature of the blood flowing past. As the blood is pumped from the left ventricle to the ascending aorta by the native cardiac function and the assistance of the pump, the thermistor detects the change in temperature and sends analog signals indicative of the change to the processor.

At step 910, a change in the motor current supplied to the pump during operation is detected. The motor current may be detected by a sensor located at the pump motor, or located externally to the pump. At step 912, the pressure in the ascending aorta is detected during pump operation. The blood pressure in the aorta is detected by a pressure sensor on the pump. The detected motor current and the detected pressure are also output to the processor.

At step 914, a first cardiac output is calculated based on the detected temperature change. The temperature change detected by the thermistor is used to calculate a total cardiac output, as described in relation to FIG. 1B and FIG. 5. In some implementations, step 914 may occur immediately after the change in temperature detected by the thermistor is transmitted to a processor, for example immediately after step 908. At step 916, pump flow is calculated based on the detected motor current and the detected pressure. The processor accesses a lookup table that provides a flow-rate for a given motor current and detected pressure. The flow rate determined from the lookup table is the pump flow output of the intravascular pump, and is indicative of the amount of assistance being provided to the heart by the pump. At step 918, the pump flow is subtracted from the first cardiac output in order to determine the native cardiac output. The native cardiac output is indicative of the output and pumping power being provided by the patient's heart itself. The native cardiac output can be used by a physician or pump operator to make therapeutic determinations, such as whether to increase or decrease assistance provided by the intravascular pump, or whether to wean the patient off of the pump's assistance. Steps 914, 916, and 918 occur in a processor coupled to the pump.

The native cardiac output, as well as other variables calculated from the first cardiac output and pump flow, can in some implementations be displayed to the physician or operator of the pump, such as on a display as depicted in FIG. 7. Providing these variables to the physician allows the physician to make informed decisions about a patient's care. The increased knowledge about the status of a patient's heart that physicians can derive and understand from these variables increases patient safety, in particular during weaning from reliance on an intravascular pump.

Figure 9:
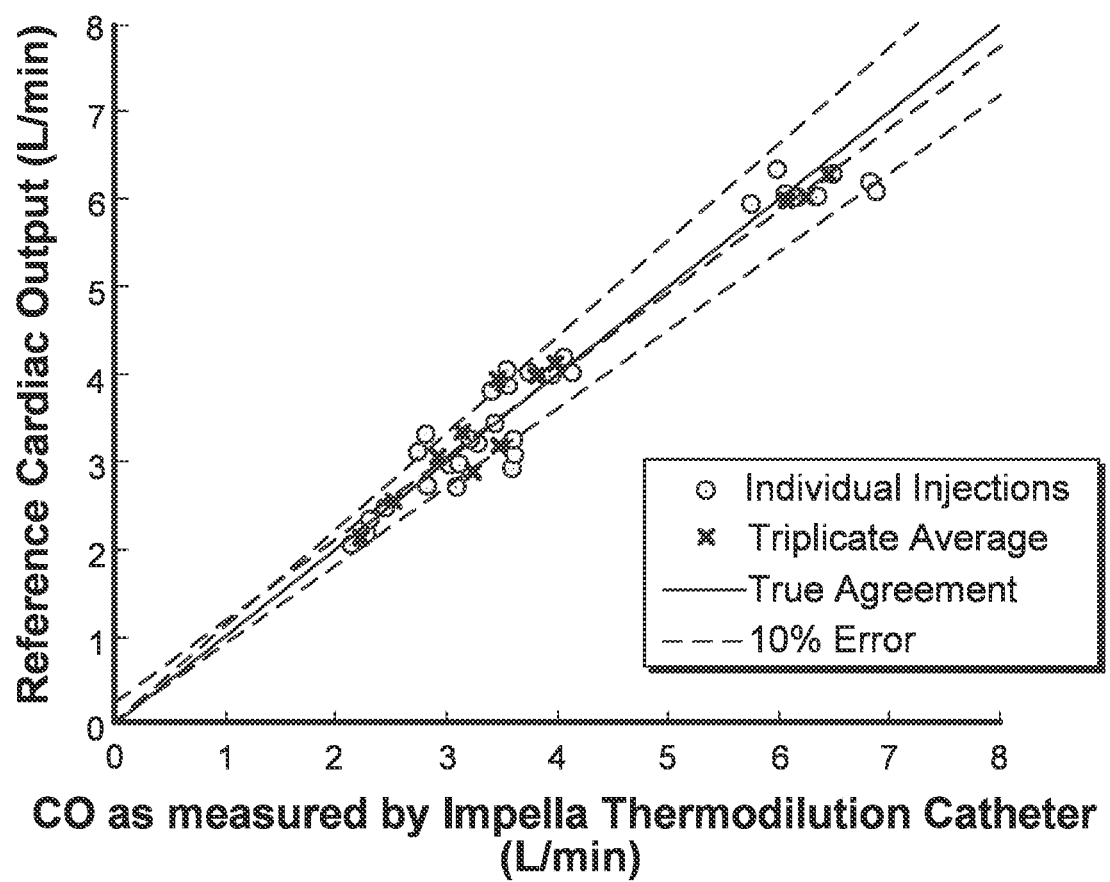
FIG. 9 illustrates cardiac output as measured by the Impella thermodilution catheter compared to a reference cardiac output measure.

FIG. 9 illustrates cardiac output as measured by the Impella thermodilution catheter compared to a reference cardiac output measure. All measurements were conducted in triplicate where the individual measurements are shown with a circle (o) and the average of each triplicate measurement is shown with a cross (x). The solid black line demarcates theoretical perfect agreement, and the dash-dot line demarcates the linear regression of all measured points. The dashed line bounds the lower and upper 10% error. As can be seen in FIG. 9, the Impella system showed good agreement over entire range of cardiac outputs measured.

Figure 10:
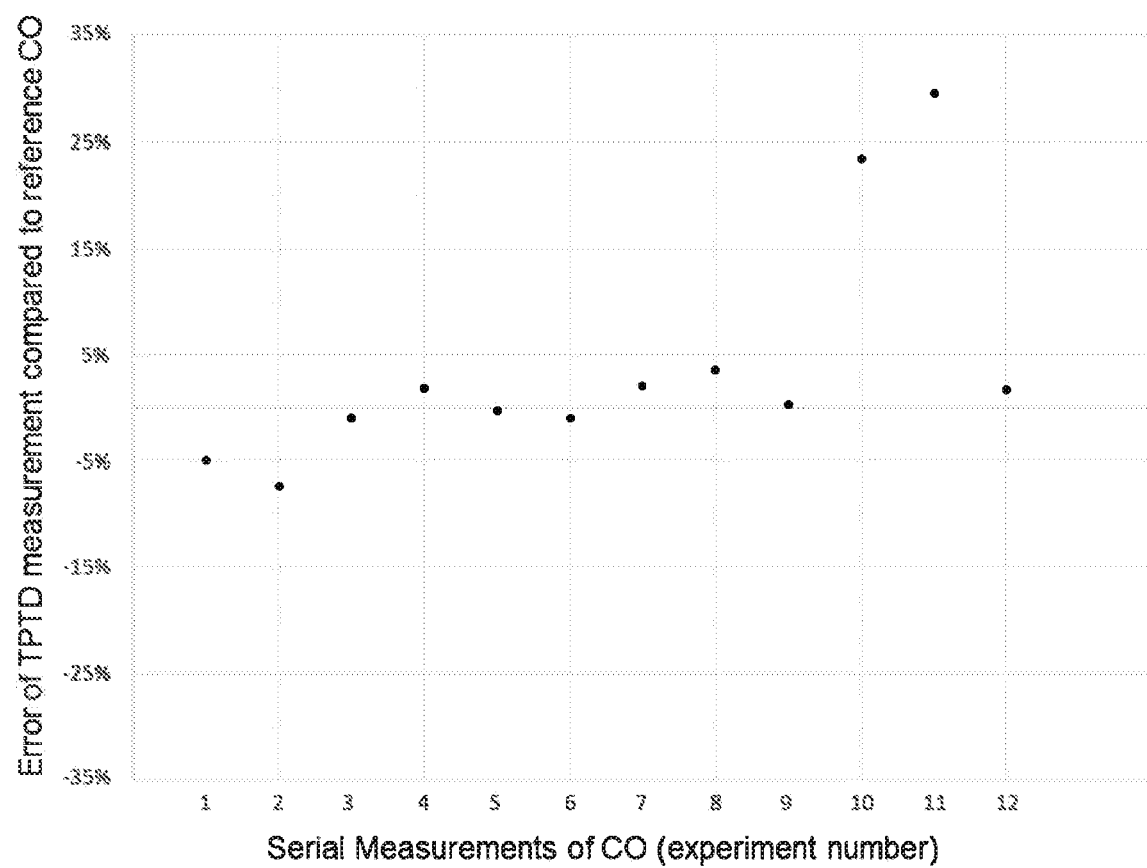
FIG. 10 illustrates the percentage error of Impella thermistor system observed in sequential experiments.

FIG. 10 illustrates the percentage error of Impella thermistor system observed in sequential experiments. Black dots represent the error of each triplicate measurement. Data is displayed in sequential order of experiment. As can be seen, the calculated error was consistent throughout sequential experiments.

Figures 11A, 11B:
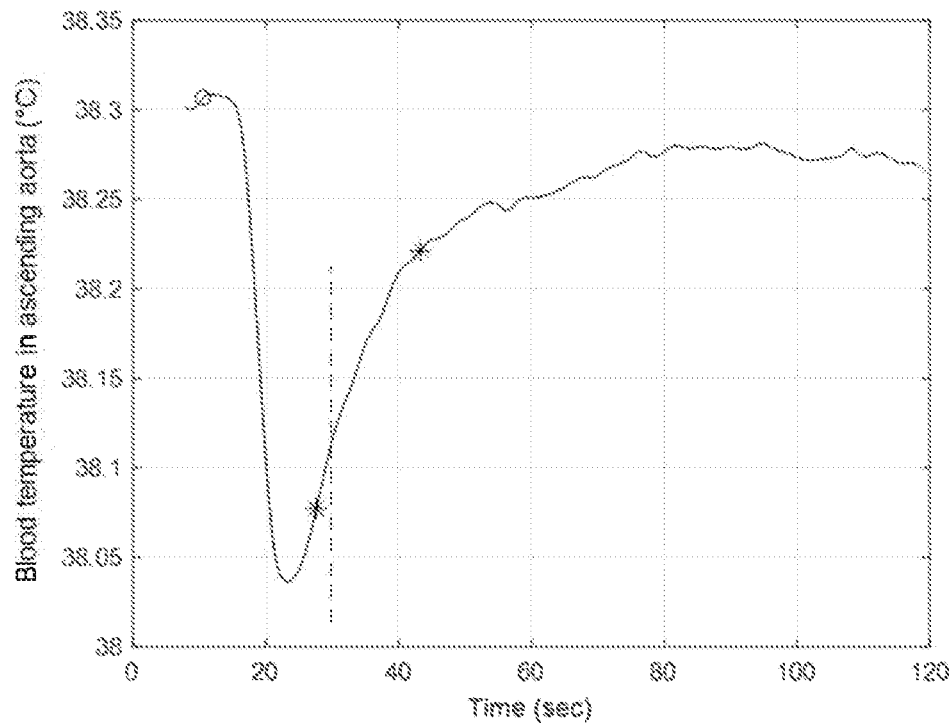
FIGS. 11A and 11B show the results obtained using the Impella thermistor system during low cardiac output.

FIGS. 11A and 11B show the results obtained using the Impella thermistor system during low cardiac output. FIG. 11A shows representative raw data trace of temperature change measured using the Impella system during low cardiac output. The open circle indicates the time of 4° C. saline injection. The dash line demarcates the time bound for the mean transit time. The portion of the curve bound by asterisks demarcates the portion of the curve used to measure downslope time. FIG. 11B shows measured and calculated variables derived from the thermodilution curve showing in FIG. 11A.

Figures 12A, 12B:
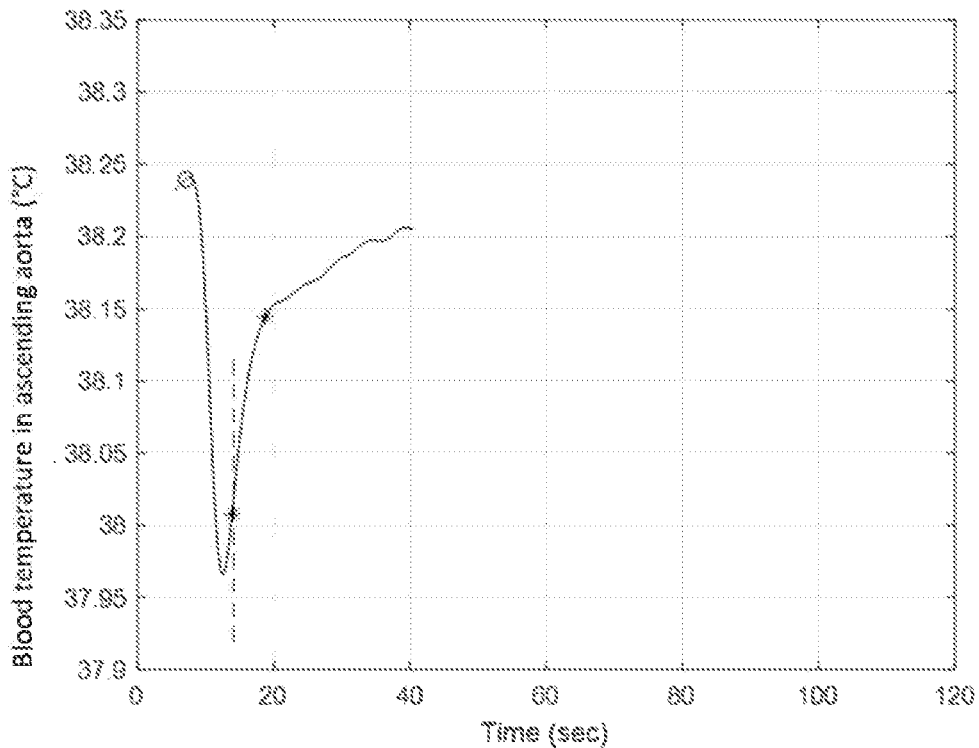
FIGS. 12A and 12B show the obtained using the Impella thermistor system during high cardiac output.

FIGS. 12A and 12B show the results obtained using the Impella thermistor system during high cardiac output. FIG. 11A shows representative raw data trace of temperature change measured using the Impella system during high cardiac output. The open circle indicates the time of 4° C. saline injection. The dash line demarcates the time bound for the mean transit time. The portion of the curve bound by asterisks demarcates the portion of the curve used to measure downslope time. FIG. 12B shows measured and calculated variables derived from the thermodilution curve showing in FIG. 12A.

Figure 13:
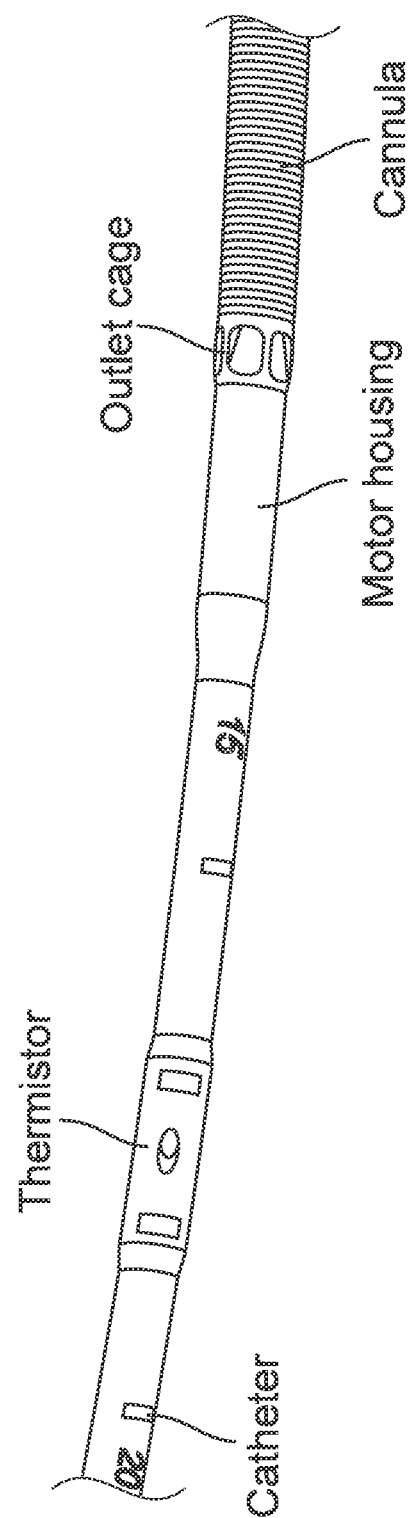
FIG. 13 illustrates placement of the thermistor in the Impella catheter and its location relative to component parts of the Impella pump.

FIG. 13 illustrates placement of the thermistor in the Impella catheter and its location relative to component parts of the Impella pump.

The foregoing is merely illustrative of the principles of the disclosure, and the methods and systems can be practiced other than the described implementations, which are represented for purposes of illustration and not of limitation. It is to be understood that the methods and systems disclosed herein, while shown for use in an intravascular blood pump system, may be applied to other cardiac assistance devices.

Variations and modifications will occur to those of skill in the art after reviewing this disclosure. For example, the positioning of the thermistor with regard to the blood pump, sheath, and catheter of the blood pump system may be arranged in any suitable manner such that the thermistor is configured to detect the change in blood temperature in the patient's heart. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitution, and alterations are ascertainable by one skilled in the art and could be made without departing from the scope of the information disclosed herein.

What is claimed is:

1. A system for measuring performance of a beating heart of a patient, comprising:
    an intracardiac blood pump having a cannula with proximal and distal openings, a surface disposed between the proximal and distal openings and being configured to be positioned in an aorta of a patient;
    an electrically driven motor and an electrical line configured to supply current to the motor to cause the intracardiac blood pump to pump blood through the cannula when the intracardiac blood pump is positioned in the aorta of the patient;
    a catheter having proximal and distal end regions, the distal end region being connected to the cannula;
    a thermistor that is configured to detect blood temperature of the blood flowing in the heart's ascending aorta when the intracardiac blood pump is positioned in the aorta of the patient;
    a first sensor configured to detect changes in the motor current during operation of the intracardiac blood pump;
    a second sensor configured to detect blood pressure within the ascending aorta when the intracardiac blood pump is positioned in the aorta of the patient; and
    a processor configured to:
        receive a first signal from the first sensor, the first signal being indicative of a change in the motor current, receive a second signal from the second sensor, the second signal being indicative of the blood pressure within the ascending aorta, and receive a third signal from the thermistor indicative of a temperature of blood flowing in the heart's ascending aorta,
        calculate a pump flow output based on the first signal and the second signal, wherein the pump flow output is indicative of a cardiac assistance provided by the intracardiac blood pump;
        calculate a total cardiac output based on the third signal, wherein the total cardiac output comprises (a) the cardiac assistance provided by the intracardiac blood pump and (b) a native cardiac output of the beating heart, and
        calculate the native cardiac output of the beating heart based on the pump flow output and the total cardiac output.

2. The system of claim 1, wherein the third signal indicates a change in temperature of blood flowing into the heart caused by a bolus of fluid introduced into vasculature of the patient at a location that is upstream from the intracardiac blood pump, wherein the introduced bolus of fluid is at an initial temperature that is different than a physiologic blood temperature.

3. The system of claim 1, wherein the third signal indicates a change in temperature of blood flowing near or through the proximal opening of the cannula.

4. The system of claim 1, wherein the processor is configured to determine the total cardiac output by detecting changes in the third signal as a function of time.

5. The system of claim 1, wherein the native cardiac output is calculated by subtracting the pump flow output from the total cardiac output.

6. The system of claim 1, wherein the thermistor is disposed on the distal end region of the catheter.

7. The system of claim 1, further comprising a second thermistor disposed on the intracardiac blood pump proximal of the proximal openings of the cannula, the second thermistor configured to detect blood temperature near the catheter.

8. The system of claim 1, wherein the processor is further configured to calculate from the first, second, and third signals at least one of a global end-diastolic volume, an intrathoracic blood volume, an intrathoracic thermal volume, a pulmonary thermal volume, a cardiac index, a stroke volume, an extravascular lung water, a cardiac power output, and a global ejection fraction.

9. The system of claim 1, wherein the processor is further configured to display the native cardiac output on a screen.

10. The system of claim 1, wherein the processor is further configured to record and store the native cardiac output and to display a history of the native cardiac output as a function of time.

11. The system of claim 10, wherein the processor is further configured to determine a native trend based on the history of the native cardiac output, wherein the native trend indicates whether the native cardiac output is improving with time.

12. The system of claim 11, wherein the processor is further configured to display the native trend on a display.

13. The system of claim 1, wherein the processor is configured to calculate the pump flow output by accessing a lookup table that provides a flow rate that is the pump flow output for a given motor current and detected pressure.

14. The system of claim 1, wherein the thermistor is positioned proximal to a proximal end of the intracardiac blood pump.

15. The system of claim 1, wherein the thermistor is imbedded in the catheter.

16. The system of claim 1, further comprising a sheath for delivering the intracardiac blood pump to the patient's heart.

17. The system of claim 16, wherein the thermistor is imbedded in the sheath.

18. The system of claim 16, wherein the sheath comprises a first lumen and a second lumen, the first lumen is sized for delivery of the intracardiac blood pump and the second lumen is sized for delivery of the thermistor.

19. The system of claim 1, further comprising a rotor disposed within the cannula.

20. A method for measuring performance of a beating heart of a patient, the method comprising:
    positioning an intracardiac blood pump in the patient's aorta and driving the intracardiac blood pump with a motor current to cause a motor of the intracardiac blood pump to pump blood from the patient's left ventricle and into the patient's ascending aorta;

detecting, by a thermistor, a change in temperature of blood being pumped from the left ventricle into the ascending aorta;

detecting, by a first sensor, a change in motor current during operation of the intracardiac blood pump;

detecting, by a second sensor, a pressure within the ascending aorta;

calculating, by a processor, a total cardiac output based on the detected temperature change wherein the total cardiac output comprises (a) a cardiac assistance provided by the intracardiac blood pump and (b) a native cardiac output of the beating heart;

calculating, by the processor, a pump flow output based on the detected change in motor current by the first sensor and the detected pressure by the second sensor, wherein the calculated pump flow output is indicative of the cardiac assistance provided by the intracardiac blood pump; and calculating, by the processor, the native cardiac output of the beating heart based on the pump flow output and the total cardiac output.

* * * * *

UNITED STATES PATENT AND TRADEMARK OFFICE
CERTIFICATE OF CORRECTION

PATENT NO. : 12,213,771 B2  
APPLICATION NO. : 17/673255  
DATED : February 4, 2025  
INVENTOR(S) : Jerald Wayne Curran, Kiyotake Ishikawa and Roger J. Hajjar It is certified that error appears in the above-identified patent and that said Letters Patent is hereby corrected as shown below:

In the Specification

Column 1, Line 8, delete "allowed" and substitute therefor --now U.S. Patent No. 11,285,310--

Signed and Sealed this
Twenty-ninth Day of April, 2025

Coke Morgan Stewart
*Acting Director of the United States Patent and Trademark Office*